United States Patent
Mohr et al.

(10) Patent No.: US 10,977,837 B2
(45) Date of Patent: Apr. 13, 2021

(54) MEDICAL IMAGE PROCESSING APPARATUS AND METHOD

(71) Applicant: CANON MEDICAL SYSTEMS CORPORATION, Otawara (JP)

(72) Inventors: Brian Mohr, Edinburgh (GB); Saad Masood, Edinburgh (GB)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 202 days.

(21) Appl. No.: 16/014,015

(22) Filed: Jun. 21, 2018

(65) Prior Publication Data

US 2019/0392614 A1    Dec. 26, 2019

(51) Int. Cl.
| | |
|---|---|
| G06T 11/00 | (2006.01) |
| G16H 30/40 | (2018.01) |
| G06K 9/62 | (2006.01) |
| G06T 7/00 | (2017.01) |
| G06T 13/20 | (2011.01) |
| A61B 5/00 | (2006.01) |
| G06T 7/38 | (2017.01) |
| A61B 5/11 | (2006.01) |

(52) U.S. Cl.
CPC .......... *G06T 11/005* (2013.01); *A61B 5/1128* (2013.01); *A61B 5/7264* (2013.01); *G06T 7/0016* (2013.01); *G06T 7/38* (2017.01); *G06T 13/20* (2013.01); *G16H 30/40* (2018.01); *G06K 9/6268* (2013.01); *G06T 2207/20081* (2013.01); *G06T 2207/30008* (2013.01)

(58) Field of Classification Search
CPC .................................................... G06K 9/6268
See application file for complete search history.

(56) References Cited

U.S. PATENT DOCUMENTS 6,975,897 B2    12/2005    Knoplioch et al.
8,923,581 B2 *  12/2014    Souza ............... G06T 7/162
                                                        382/128

(Continued)

FOREIGN PATENT DOCUMENTS

JP    2013-192646    9/2013
JP    2017-299    1/2017

OTHER PUBLICATIONS

Lower Limb / Radiology Key, Fastest Radiology Insight Engine (http://radiologykey.com/lower-limb-3/), obtained on Apr. 30, 2018, 21 pages.

(Continued)

*Primary Examiner* — King Y Poon
(74) *Attorney, Agent, or Firm* — Oblon, McClelland, Maier & Neustadt, L.L.P.

(57) ABSTRACT

A medical image processing apparatus comprises processing circuitry configured to: acquire a series of medical imaging data sets acquired across multiple time phases, wherein the medical imaging data sets are representative of a first body part and a second body part in the vicinity of the first body part, and wherein the first body part and second body part undergo relative motion across the multiple time phases; and automatically determine a viewing surface for rendering a series of images from the medical imaging data sets, wherein the determining of the viewing surface is based on respective positions of the first body part and second body part in each of the series of medical imaging data sets.

18 Claims, 7 Drawing Sheets

(56) References Cited

U.S. PATENT DOCUMENTS

| | | | |
|---|---|---|---|
| 2002/0147329 A1* | 10/2002 | Luyten | C07K 14/71 |
| | | | 536/23.5 |
| 2005/0195190 A1 | 9/2005 | Williams et al. | |
| 2008/0212856 A1* | 9/2008 | Oosawa | G06F 19/321 |
| | | | 382/128 |
| 2010/0239140 A1 | 9/2010 | Ruijters et al. | |
| 2012/0026162 A1 | 2/2012 | Masumoto | |
| 2012/0099804 A1* | 4/2012 | Aguilera | G06T 15/20 |
| | | | 382/285 |
| 2013/0085723 A1 | 4/2013 | Chabanas et al. | |
| 2016/0171698 A1 | 6/2016 | Razeto et al. | |
| 2016/0361038 A1* | 12/2016 | Fujiwara | A61B 6/466 |

OTHER PUBLICATIONS

G. Elisabeta Marai et al., "A Kinematics-Based Method for Generating Cartilage Maps and Deformations in the Multi-Articulating Wrist Joint From CT Images", Proceedings of the 28th IEEE EMBS Annual International Conference New York City, USA, Aug. 30-Sep. 3, 2006, 4 pages.

\* cited by examiner

US 10,977,837 B2

MEDICAL IMAGE PROCESSING APPARATUS AND METHOD

FIELD

Embodiments described herein relate generally to a method of, and apparatus for, image processing of medical imaging data. Embodiments have, for example, application for visualizing motion of a joint.

BACKGROUND

There is a clinical need to understand and analyze a joint while it is in motion. Certain orthopedic pathologies may only manifest when a joint is in motion.

It is known to acquire four-dimensional (4D) medical imaging data that is representative of motion, for example motion of a joint. The 4D medical imaging data is representative of three spatial dimensions plus time. A 4D acquisition may be displayed as an animated sequence of a three-dimensional (3D) view.

Certain 4D orthopedic applications provide an advanced feature to lock a bone or set of bones in one place over a full series of images. A bone or set of bones may be given a constant position, orientation and/or projection in a 3D view over an animated sequence.

In one 4D application, a series of volumes represents a movement of a plurality of bones including a locked set of bones (for example, movement of one or more joints). Each of the series of volumes may be rendered to provide a respective frame of an animated display showing the movement. The animated display is rendered such that the locked set of bones are held static across all frames, and other bones are presented as moving relative to the locked set of bones.

By rendering an animated display such that one or more bones are held static, a clinician may obtain additional information about the relative position of the bones that may not be available if each image was rendered in its original position. By holding one or more bones static, it may be easier to see the relative motion between those bones and a further bone or bones, which may give insight into any problems with the motion and may be helpful in describing the dynamics of the surrounding bones and ligaments.

The presentation of images in which motion occurs relative to one or more locked bone may be referred to generally as bone locking. Locking bones in one place may also be referred to as fixing the bones.

A user may navigate through a series of volumes (which may be referred to as a 4D bone locked stack) using standard views, for example multi-planar reconstruction (MPR) and oblique views.

The wrist is one of the most intricate articulations of the musculoskeletal system. The wrist comprises eight small bones (the carpal bones) and a complex intrinsic and extrinsic ligament system. FIG. 1 shows the eight small carpal bones 10A to 10H together with parts of the radius 12 and ulna 14 (the bones of the forearm). FIG. 1 also shows parts of the metacarpal bones 16. Because of the complexity of the wrist, injuries to the bones or ligaments of the wrist may potentially cause irreversible disruption to the movement of the wrist, and may initiate progressive osteoarthritis.

It is known to study the movement of the wrist by taking a series of images of the wrist, each image being taken with the wrist at a different position. For example, the wrist may be moved such that the hand moves from side to side in the plane of the hand, as in a waving motion (this motion may be referred to as radial-ulnar deviation). The movement of the wrist may be studied to provide a comparison of the movement pre- and post-treatment, for example to determine a change in movement due to surgery.

If a series of images of the wrist are rendered without bone locking, such that all bones and joints are in motion, it may be difficult for a user to interpret the images. For example, it may be difficult for a user to assess relative movement of a pair of bones when both of the bones are moving.

The use of bone locking may enable a user to better interpret joint motion. For example, it may be easier to interpret the relative movement of a pair of bones when one of those bones is locked, and the movement of the other bone is displayed relative to the locked bone.

When viewing images of a joint, a user may choose which view to use. For example, the user may choose a plane on which to perform multi-planar reconstruction. The user may manually change the plane in order to obtain the best view of the joint. For example, the user may wish to see gaps between bones in the joint, and so may attempt to choose the plane that best shows the gaps between bones.

In some circumstances, it may be difficult for a user to manually navigate through a 4D bone-locked stack to find a good plane to observe multiple joints. For example, the best plane for viewing one frame of a series may not be the same as the best plane for viewing another frame of the series. It may therefore be difficult to find a plane that produces an acceptable result for all of the frames in the series.

Manually navigating through the 4D bone-locked stack to find a good plane may be time-consuming. Manually navigating through the 4D bone-locked stack to find a good plane may be especially challenging for 4D acquisitions in which the range of motion is not very planar. Bending the fingers or twisting the wrist may be examples of non-planar motion.

BRIEF DESCRIPTION OF DRAWINGS

Embodiments are now described, by way of non-limiting example, and are illustrated in the following figures, in which.

DETAILED DESCRIPTION

Certain embodiments provide a medical image processing apparatus comprising processing circuitry configured to: acquire a series of medical imaging data sets acquired across multiple time phases, wherein the medical imaging data sets are representative of a first body part and a second body part in the vicinity of the first body part, and wherein the first body part and second body part undergo relative motion across the multiple time phases; and automatically determine a viewing surface for rendering a series of images from the medical imaging data sets, wherein the determining of the viewing surface is based on respective positions of the first body part and second body part in each of the series of medical imaging data sets.

Certain embodiments provide a medical image processing method comprising: acquiring a series of medical imaging data sets acquired across multiple time phases, wherein the medical images are representative of a first body part and a second body part in the vicinity of the first body part, and wherein the first body part and second body part undergo relative motion across the multiple time phases; and automatically determining a viewing surface for rendering a series of images from the medical imaging data sets, wherein the determining of the viewing surface is based on respective positions of the first body part and second body part in each of the series of medical imaging data sets.

Certain embodiments provide a medical image processing apparatus comprising processing circuitry configured to: acquire at least one medical imaging data set representative of a first body part and a second body part in the vicinity of the first body part; identify at least one articular surface between the first body part and the second body part; and determine a viewing surface for rendering at least one medical image from the at least one medical imaging data sets, wherein the determining of the viewing surface is based on the at least one articular surface.

Certain embodiments provide a medical imaging processing apparatus comprising processing circuitry configured to: acquire at least one medical imaging data set representative of a first body part and multiple second body parts in the vicinity of the first body part; and determine a viewing surface for rendering at least one image from the at least one medical imaging data set, the viewing surface comprising a plurality of planar viewing sections having different orientations, each of the planar viewing sections corresponding to a respective one of the second body parts.

Figure 1:
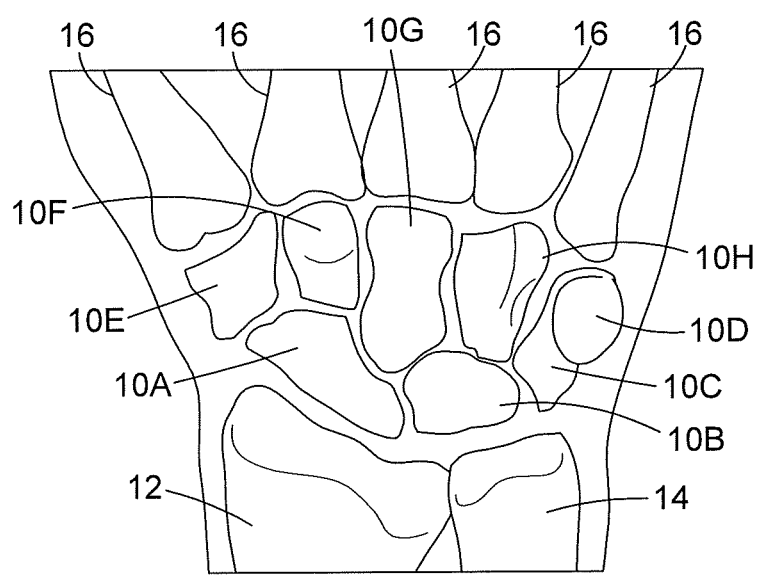
FIG. 1 is a schematic illustration of the wrist.
Figure 2:
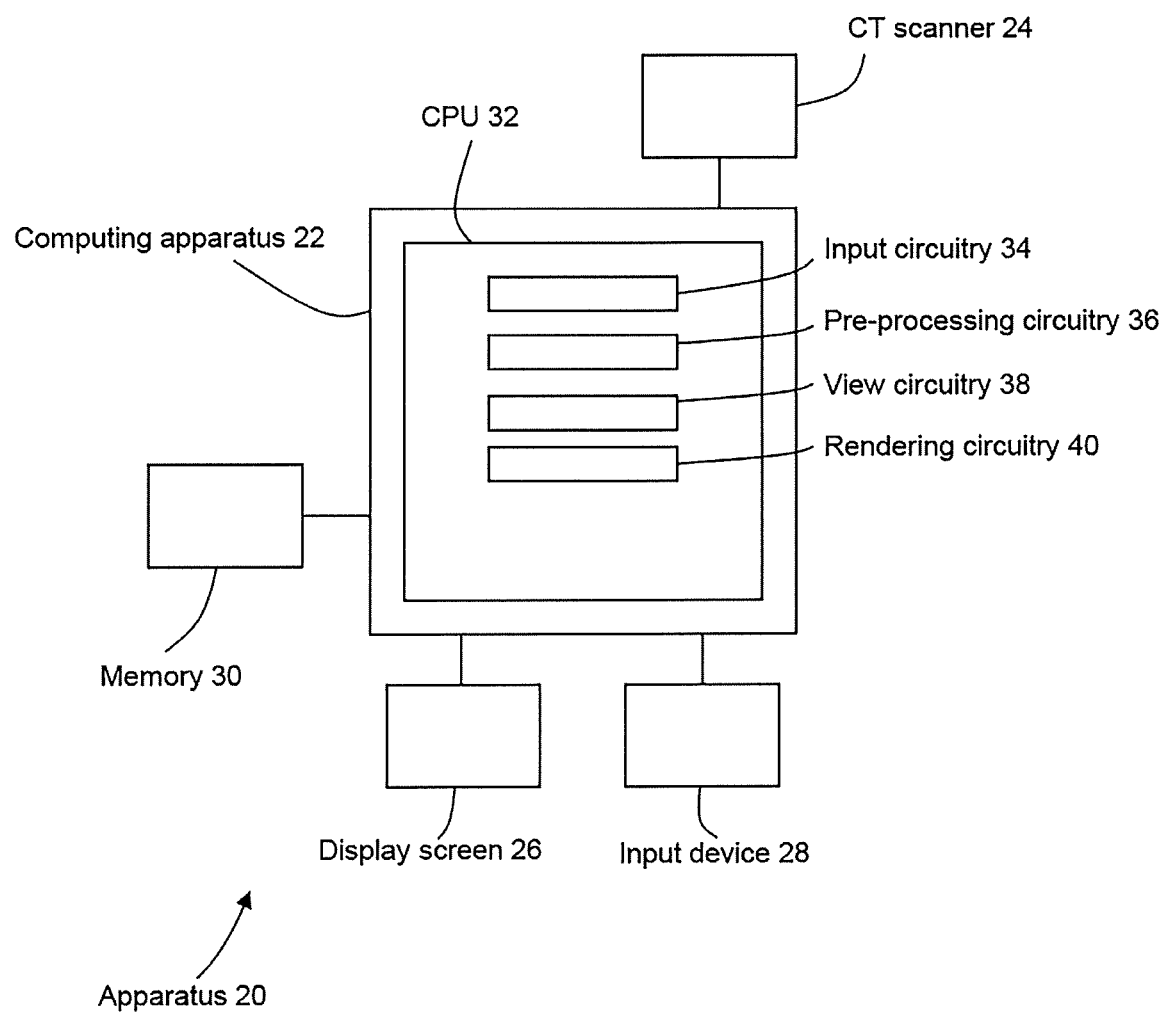
FIG. 2 is a schematic illustration of an apparatus according to an embodiment.

A medical imaging data processing apparatus 20 according to an embodiment is illustrated schematically in FIG. 2. The imaging data processing apparatus 20 comprises a computing apparatus 22, in this case a personal computer (PC) or workstation, which is connected to a CT scanner 24, one or more display screens 26 and an input device or devices 28, such as a computer keyboard, mouse or trackball.

The CT scanner 24 may be any CT scanner that is configured to obtain volumetric medical imaging data of a region of a patient. In the present embodiment, the region of the patient is a wrist. The volumetric medical imaging data comprises multiple medical imaging data sets, each of which corresponds to a scan of the wrist at a different time phase while the wrist is in motion. Each volumetric imaging data set is therefore representative of the wrist in a different position.

In other embodiments, the region of the patient may be any appropriate region, for example any joint such as a wrist, ankle, knee, elbow or neck. Although in this description we may at times refer to the wrist as one joint, the wrist may also be considered to be a combination of multiple individual joints, where each joint comprises at least two bones which interact with each other. In further embodiments, the volumetric medical imaging data may be representative of any suitable body parts.

In alternative embodiments, the CT scanner 24 may be replaced or supplemented by a scanner in any other imaging modality, for example an MRI (magnetic resonance imaging) scanner, ultrasound scanner, Cone Beam CT scanner, C-Arm X-ray scanner able to perform rotational X-ray, or any other scanner capable of obtaining four-dimensional (4D) medical imaging data.

In the present embodiment, volumetric image data sets obtained by the CT scanner 24 are stored in memory 30 and subsequently provided to computing apparatus 22. In an alternative embodiment, image data sets are supplied from a remote data store (not shown) which may form part of a Picture Archiving and Communication System (PACS). The memory 30 or remote data store may comprise any suitable form of memory storage.

Computing apparatus 22 provides a processing resource for automatically or semi-automatically processing image data sets, and comprises a central processing unit (CPU) 32.

The computing apparatus 22 includes input circuitry 34 for receiving volumetric imaging data and user input, pre-processing circuitry 36 for articular surface extraction and bone locking, viewing circuitry 38 for determining a viewing surface comprising at least one viewing plane, and rendering circuitry 40.

In the present embodiment, the various circuitries are each implemented in the CPU and/or GPU of computing apparatus 22 by means of a computer program having computer-readable instructions that are executable to perform the method of the embodiment. However, in other embodiments each circuitry may be implemented in software, hardware or any suitable combination of hardware and software. In some embodiments, the various circuitries may be implemented as one or more ASICs (application specific integrated circuits) or FPGAs (field programmable gate arrays).

The computing apparatus 22 also includes a hard drive and other components of a PC including RAM, ROM, a data bus, an operating system including various device drivers, and hardware devices including a graphics card. Such components are not shown in FIG. 2 for clarity.

The system of FIG. 2 is configured to perform the method of embodiments that are described below with reference to FIG. 3.

Figure 3:
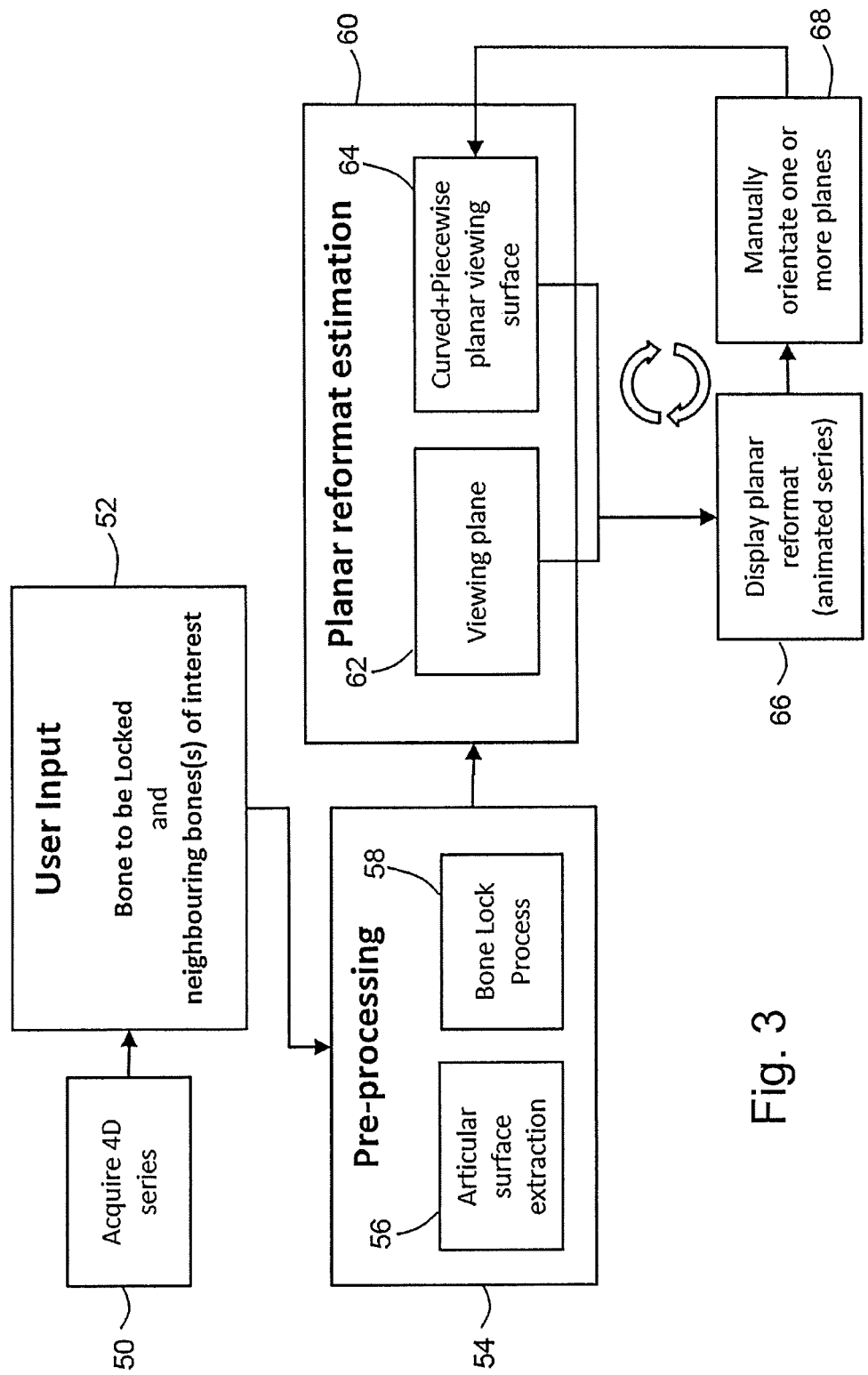
FIG. 3 is a flow chart illustrating in overview a process performed in accordance with an embodiment.

FIG. 3 is a flow chart illustrating in overview the method of two embodiments. In a first embodiment, a viewing surface comprising a single viewing plane is determined for a 4D bone-locked stack comprising medical imaging data sets corresponding to multiple time phases. In a second embodiment, a viewing surface comprising piecewise planar sections is determined for the 4D bone-locked stack. In each of the embodiments, an image is rendered using the determined viewing surface to obtain a desired view of a joint represented in the 4D bone-locked stack. Each of the two embodiments of FIG. 3 is described in turn below.

We consider first the embodiment in which a viewing surface consisting of a single viewing plane is determined.

At stage 50 of FIG. 3, the input circuitry 34 receives a series of volumetric medical imaging data sets, each of which corresponds to a respective frame of a 4D sequence. In the present embodiment, the series of volumetric imaging data sets is obtained from a CT scan of a radial-ulnar motion of the wrist of a patient. The series may also be referred to as a time series. The volumetric imaging data sets are representative of scans taken at different times during the motion of the wrist, which are referred to as different time phases. Each of the volumetric imaging data sets is representative of a particular position of the wrist. The positions of the wrist cover the full range of motion of the wrist in the radial-ulnar sense.

In other embodiments, the 4D sequence may be obtained using any suitable modality. The 4D sequence may be representative of any body parts that are in relative motion, for example any suitable movement of any suitable joint or joints.

At stage 52 of FIG. 3, the input circuitry 34 receives from a user an indication of a bone that is to be locked, which is denoted as $B_{lock}$. The bone to be locked may also be referred to as the first bone, or as a user-selected bone. In other embodiments, the user may provide an indication of multiple bones to be locked. In some embodiments, multiple bones or joint may be locked with respect to each other.

The user may indicate the bone to be locked using any suitable method. For example, an image rendered from a frame of the 4D sequence may be displayed to the user, and the user may select the bone to be locked by clicking on or otherwise highlighting a bone in the displayed image. Alternatively, the user may provide the name of the bone.

In other embodiments, a bone to be locked may be identified before the process of FIG. 3 commences. For example, the input circuitry 34 may store instructions comprising details of which of the bones in a given joint (for example, the wrist) is to be locked. A bone or bone to be locked may be specified as part of a hanging protocol or clinical workflow.

In some embodiments, the pre-processing circuitry 36 processes at least one of the volumetric data sets to obtain an indication of the bone that is to be locked, $B_{lock}$. For example, the pre-processing circuitry 36 may know (for example, from a user or from stored data) the name of a bone that is to be locked. The pre-processing circuitry 36 may obtain an indication of the bone to be locked in the volumetric imaging data sets by any suitable method, for example by registering at least one of the volumetric data sets to an atlas; by estimating at least one bone landmark; or using a learned classification method.

In the present embodiment, the input circuitry 34 also receives from the user an indication of one or more neighboring bones of interest which are in the vicinity of the locked bone. The neighboring bone or bones of interest may be denoted by $[B_1 \ldots B_N]$, or may be referred to as second bones. For example, the user may select other bones of the joint (other than the bone to be locked) as being neighboring bones of interest. In some embodiments, the user may select bones that are not part of the joint. In further embodiments, the user may select any body parts that are in relative motion with the locked bone (or other locked body part).

In some embodiments, the volumetric imaging data sets may be representative of multiple joints. The user may select bones that are part of a different joint from the joint that comprises the bone to be locked.

The user may select the neighboring bone or bones of interest using any suitable method. In other embodiments, the neighboring bone or bones of interest may be identified before the process of FIG. 3 commences. In further embodiments, the pre-processing circuitry 36 may process at least one of the volumetric data sets to obtain an indication of the neighboring bone or bones of interest, for example using any of the methods listed above in respect of the indication of the bone to be locked.

At the completion of stage 52, the input circuitry 34 passes the identification of the bone to be locked $B_{lock}$ and the neighboring bones of interest $[B_1 \ldots B_N]$ to the pre-processing circuitry 36. The locked bone $B_{lock}$ and the neighboring bones of interest $[B_1 \ldots B_N]$ may together be referred to as display targets, since they are bones that have been selected by the user for display in rendered images.

The pre-processing circuitry 36 performs a pre-processing stage 54 which comprises an articular surface extraction sub-stage 56 and a bone lock process sub-stage 58.

The articular surface extraction sub-stage 56 comprises extracting bone articular surfaces for $B_{lock}$ and for $[B_1 \ldots B_N]$ using a precomputed bone articular surface map. In the present embodiment, the joint of interest is the wrist, so the pre-processing circuitry 36 uses an precomputed bone articular surface map that is specific to the wrist.

In other embodiments, any suitable method may be used to obtain bone articular surfaces. For example, the bone articular surfaces may be determined using a bone landmark estimation method. The bone articular surfaces may be determined using a learned classification algorithm and/or regression algorithm. The bone articular surfaces may be derived using image analysis techniques directly from the acquired data.

In some embodiments, bone articular surfaces are determined using bone segmentation. In some embodiments, bone segmentation is used with a combination of morphology to determine the surface and surface distances to identify the articulate surfaces. Distance may be used as a heuristic. Any suitable method of bone segmentation may be used.

Figures 4A, 4B:
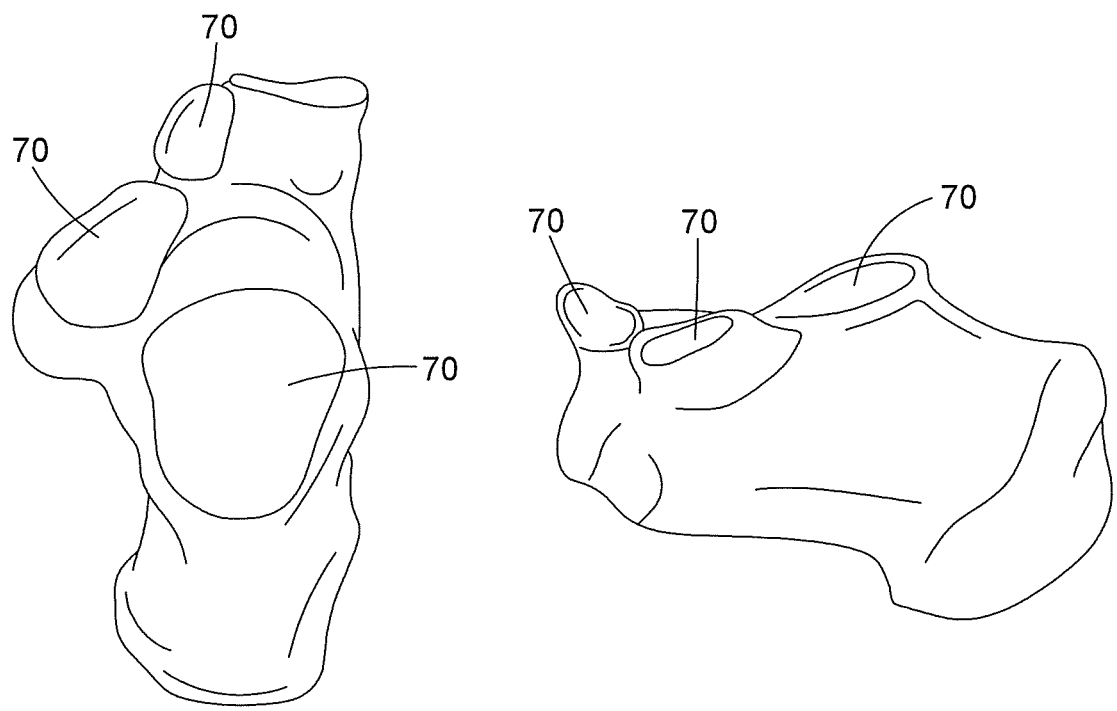
FIG. 4a is a schematic illustration of a bone showing the articular surfaces.
FIG. 4b is a schematic illustration of a bone showing the articular surfaces.

An articular surface is a bone surface region where a bone forms an interface with another bone. For example, a part of the surface of a bone that faces another bone with which it interacts in a joint may be considered to be an articular surface. A given bone may have one or more articular surfaces, depending on how many other bones it interacts with. An example of a bone having articular surfaces is shown in FIGS. 4a and 4b, which are schematic illustrations showing articular surfaces 70 of the right calcaneus (heel bone). FIG. 4a shows the superior aspect of the right calcaneus. FIG. 4b shows the medial aspect of the right calcaneus.

An articular surface map stores a respective label for each location in the bones of the anatomy of interest (in this embodiment, the wrist). Each location in the bones of the anatomy of interest is labelled as either articular surface or non-articular surface. The articular surface map provides data on which locations of bone surfaces are involved in a joint (for example, which locations interact with other bones), and which are not.

In some embodiments, the articular surface map is specialized to a certain type of motion, for example radial-ulnar flexion or pronation-supination. The articular surfaces that are identified in the articular surface map may include only articular surfaces that are involved in the selected type of motion.

Figure 5:
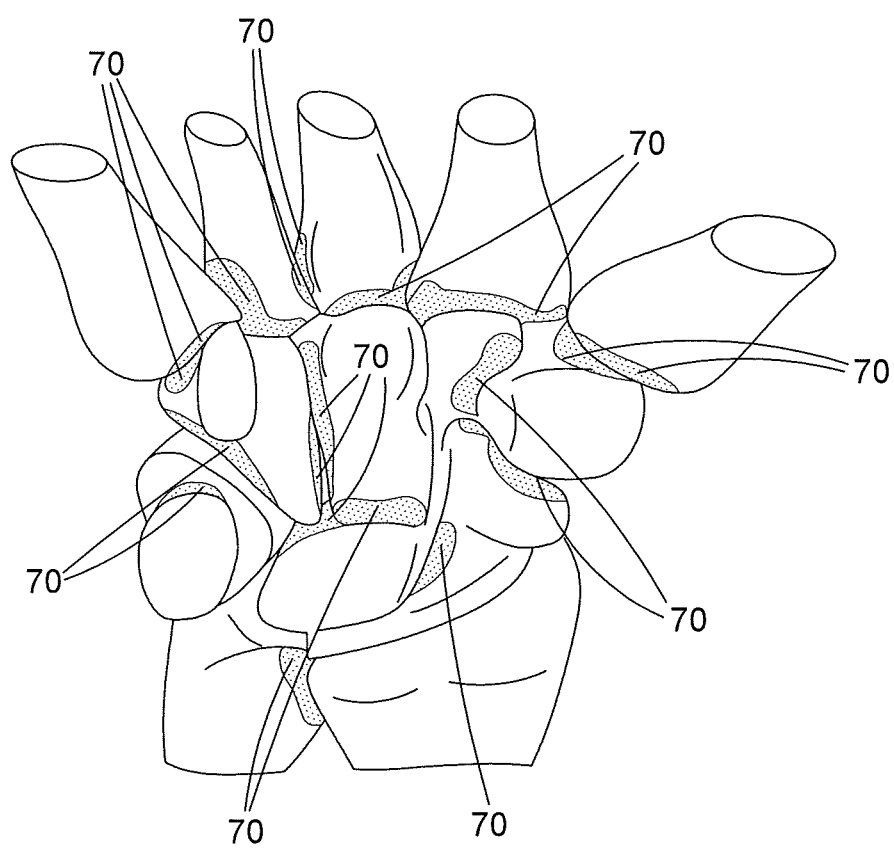
FIG. 5 is a schematic illustration of an articular surface map.

FIG. 5 is a schematic illustration of an articular surface map. Regions 70 are articular surfaces. Although it may be difficult to see from the orientation of FIG. 5, the articular surfaces are arranged in facing pairs, with articular surfaces occurring between interacting bones. For each pair of bones that interact with each other, a first bone of the pair of bones has a first articular surface, and a second bone of the pair of bones has a second articular surface that faces the first articular surface.

The interaction of bones may be of interest to a clinician who is assessing joint motion. The gaps between bones (for example, between bones of a joint that interact with each other) may be of interest to the clinician. Therefore, the identifying of articular surfaces may identify areas that may be of interest to the clinician.

The pre-processing circuitry 36 registers a selected one of the volumetric imaging data sets with the articular surface map. In the present embodiment, the pre-processing circuitry 36 registers the one of the volumetric imaging data sets that is closest to a position that may be described as neutral phase. In the neutral phase of motion, the position of the wrist may be closest to a standard anatomical position that is represented in the articular surface map. In other embodiments, any or all of the volumetric imaging data sets may be registered with the articular surface map.

The pre-processing circuitry 36 uses the labels of the articular surface map to label the articular surfaces of the bones in the volumetric imaging data set, based on the registration.

In the present embodiment, each articular surface is considered to have a width of one voxel. The pre-processing circuitry 36 labels each location on the articular surface by labelling the voxel that most closely describes the position of the articular surface (which may be considered as a floating point surface).

In the present embodiment, the registration of the volumetric imaging data sets and the articular surface map is performed using a method as described in U.S. patent application Ser. No. 14/569,890, which is hereby incorporated by reference. In other embodiments, any suitable registration method may be used, for example any suitable non-rigid registration.

The output of sub-stage 56 is a version of the selected volumetric imaging data set in which the relevant articular surfaces of the bones in the joint are labelled.

In the present embodiment, the articular surface map labels locations as articular surface or non-articular surface. In other embodiments, the articular surface map may use different labels for different articular surfaces. For example, different labels may be used for articular surfaces of different bones. In some embodiments, different labels may be used for different articular surfaces of the same bone.

At stage 58, the pre-processing circuitry 36 performs a bone locking process. The pre-processing circuitry 36 estimates the centroid of the locked bone $B_{lock}$ in the selected one of the volumetric imaging data set. The centroid is used as a reference point for the locked bone $B_{lock}$. Any suitable method may be used to estimate the centroid of the locked bone $B_{lock}$. In other embodiments, any reference point or region within the locked bone may be identified. In such embodiments, the identified reference point may not be the centroid.

The pre-processing circuitry 36 registers the other ones of the volumetric imaging data sets to the selected volumetric imaging data set. The registration is performed such that the position of the locked bone remains static in each of the frames. Any suitable method of registration may be used, for example any suitable rigid registration. In the present embodiment, the registration is as described in U.S. patent application Ser. No. 14/569,890. The pre-processing circuitry 36 propagates the articular surface labels to each of the volumetric imaging data sets based on the registrations between the selected volumetric imaging data set and the other volumetric imaging data sets.

In further embodiments, each one of the volumetric imaging data sets may be individually registered with the articular surface map. The labelling of the articular surfaces in each of the volumetric imaging data sets may be based on the registration of that volumetric imaging data set to the articular surface map. The bone locking process may be performed separately from the propagation of the articular surface labels.

The output of sub-stage 58 (and therefore the output of stage 54) is a registered set of volumetric imaging data sets in which the position of the locked bone $B_{lock}$ is static. Articular surfaces of interest are identified in each of the volumetric imaging data sets.

The process of FIG. 3 proceeds to stage 60, which may be referred to as a planar reformat estimation stage. Stage 60 comprises two alternative versions, which are shown as sub-stage 62 and sub-stage 64. Sub-stage 62 is used in the present embodiment. Sub-stage 64 is described in relation to a later embodiment.

At sub-stage 62, the viewing circuitry 38 performs an automatic determination of a single planar surface, which may be referred to as a viewing plane, view plane, linear view plane, or linear viewing plane. The viewing plane is a flat 2D surface. In the present embodiment, the viewing plane extends through the whole of the volume represented by the volumetric imaging data sets. In other embodiments, the viewing plane may be limited to a region of interest, for example a joint of interest. In some embodiments, the extent of the viewing plane is constrained by the position and extent of the locked bone $B_{lock}$ and the neighboring bones $[B_1 \ldots B_N]$.

In the present embodiment, the viewing plane is constrained such that it contains the centroid of the locked bone $B_{lock}$. The viewing plane is constrained to intersect the centroid of the locked bone $B_{lock}$. In other embodiments, the viewing plane may be constrained to pass through any suitable reference point or region in the locked bone. In further embodiments, the viewing plane may be constrained to pass within a predetermined distance of a reference point (for example, the centroid) or region in the locked bone. In further embodiments, the viewing plane may be constrained to pass through at least part of the locked bone. In other embodiments, the viewing plane may not be constrained by the locked bone.

The viewing circuitry 38 determines the viewing plane using a process which may be described as an optimization process. The viewing plane is determined based on the articular surfaces in the volumetric imaging data sets, which have now been registered with each other such that the position of the locked bone $B_{lock}$ remains static throughout the volumetric imaging data sets.

In the optimization process, the viewing circuitry 38 fits the viewing plane to the volumetric imaging data sets so as to maximize the projection of coordinate points on the articular surfaces onto the viewing plane. The optimization is dependent on the position of the articular surfaces of the bones in the volumetric imaging data sets. In other embodiments, any optimization process may be used that is dependent on position of bones in the volumetric imaging data sets.

In the present embodiment, the viewing circuitry 38 considers multiple possible orientations of the viewing plane, while constraining the viewing plane to pass through the center of the locked bone. For each of the orientations, the viewing circuitry 38 projects the 3D articular surfaces onto the viewing plane. Each articular surface is assumed to have a width of one voxel. Each articular surface comprises a plurality of coordinate points which are the nearest voxels to the position of the articular surface when the surface is considered as floating point. The coordinate points of the articular surface are projected onto the viewing plane.

The projection results in a 2D shape on the viewing plane. It may be that some of the 3D coordinate points on the articular surface have projections on to the plane that overlap with the projections of other 3D coordinate points. Therefore, it may be the case that not all of the 3D coordinate points on the articular surface uniquely contribute to the projected shape on the viewing plane.

In the present embodiment, only projections for which the viewing plane is within the extent of the bone are counted. Any projection that reaches the viewing plane outside the bone bounds is excluded.

The viewing circuitry 38 sums the number of coordinate points on the articular surfaces which are projected onto the viewing plane. In other embodiments, the viewing circuitry 38 may sum the number of coordinate points in the 2D projected shape on the viewing plane.

The sum is across all of the volumetric imaging data sets. The viewing circuitry 38 selects the orientation for the viewing plane for which the sum is the highest. The selected viewing plane is the viewing plane for which the greatest number of articular surface coordinate points are projected onto the viewing plane, when all of the volumetric imaging data sets are considered.

Since the sum is across all of the volumetric imaging data sets, the viewing circuitry 38 may favor orientations of the viewing plane for which the viewing plane passes through the bones in all (or nearly all) of the volumetric imaging data sets.

The use of the projection here may allow voxels of the articular surfaces that do not lie on the plane to have some more influence on the outcome of the optimization. Over the entire 4D set of volumetric data sets there may be a number of surfaces that do not overlap (where the term overlap is used to indicate intersection of the articular surface with the plane over the set of volumes). The use of the projection may help the optimization find the most overlap.

In some cases, the viewing plane will not intersect with the articular surface for a given volume. The projections (depending on how it may be constrained) may potentially reach the plane and thus include the information from all the volumes. In other cases, the projection may not reach the plane in some volumes, for example the projection is constrained to only contribute when the plane is within the bone bounds.

The projection may be considered to be a projection over the entire 4D sequence, space and time.

The optimization process comprises a fit to maximize the projection of bone articular surface points over all the volumetric imaging data sets in the registered 4D sequence.

In other embodiments, the viewing circuitry 38 may fit the viewing plane using any function that is representative of a projection of points on the articular surfaces onto the linear viewing plane. In some embodiments, the function is weighted, for example to favor particular articular surfaces and/or particular phases of motion. Any suitable measure or combination of measures may be used to determine the viewing plane.

In further embodiments, the viewing circuitry 38 uses the intersection of the viewing plane with each of the articular surfaces. The viewing circuitry counts the number of articular surface coordinate points that lie on the viewing plane. The optimization process is performed to maximize the intersection of the linear viewing plane with the articular surfaces in each of the volumetric imaging data sets.

In further embodiments, the viewing circuitry 38 fits a slab rather than a single plane. The viewing circuitry 38 may fit an orientation of the slab by projecting points on the articular surface on to the slab, for example using a projection method as described above. The viewing circuitry 38 may fit an orientation of the slab using points on the articular surface that lie within the slab.

In other embodiments, any suitable method may be used to determine a viewing plane that crosses a reference point (for example, the centroid) of a first body part and includes at least part of an articular surface between the first body part and at least one second body part, through multiple time phases. In further embodiments, no reference point is specified.

Once the viewing plane has been determined by the viewing circuitry 38, the rendering circuitry 40 renders each of the volumetric imaging data sets to obtain a respective frame of an animated series. In the present embodiment, the rendering comprises a planar reformat using the viewing plane. In other embodiments, any suitable method may be used for rendering using the viewing plane.

Each of the volumetric imaging data sets is rendered using the same viewing plane, which is the viewing plane that was determined at stage 62. The output of the rendering process is a series of rendered images, one for each of the volumetric imaging data sets. The rendered images may be referred to as frames. The frames may be combined to provide an animation showing the motion of the joint (in this embodiment, the wrist).

In the present embodiment, each rendered frame shows only the locked bone $B_{lock}$ and neighboring bones $[B_1 \ldots B_N]$ that were selected by the user. The display position of the locked bone $B_{lock}$ is fixed through the multiple time phases.

In other embodiments, other bones and/or further anatomical features that are not bones may be shown in the rendered frames.

The rendering circuitry 40 may also render further images from the volumetric imaging data sets. For example, the rendering circuitry 40 may render an image using at least one plane that is orthogonal to the viewing plane. In some circumstances, the viewing plane may be the plane of the motion of the joint of interest. The orthogonal plane or planes may be orthogonal to the plane of motion.

At stage 66, the animated series of frames that was rendered at sub-stage 62 is displayed to a user. Other images may also be displayed, for example images rendered in at least one orthogonal plane.

The position of the locked bone remains static in the rendered frames. The locked bone has a consistent appearance across the rendered frames. Neighboring bones may appear to move relative to the locked bone when moving through the series of rendered frames, for example when viewing the frames as an animation.

Articular surfaces are the surfaces at which bones interact. The interaction of the bones may be of interest to a clinician. In particular, the clinician may be interested in observing a gap between the articular surfaces, for example how that gap changes with motion. By fitting the viewing plane using articular surfaces, images may be obtained that have a good view of a gap between articular surfaces. By fitting the viewing plane using all of the volumetric imaging data sets, the gap may be visible across most or all of the rendered frames, which may be useful to the clinician. It may be difficult for a clinician to manually find a viewing plane orientation in which the gap is visible across most or all of the rendered frames.

At stage 68, the user has the option to manually adjust the viewing plane that was determined by the viewing circuitry 38. If the user chooses to manually adjust the viewing plane, the process returns to stage 60. At sub-stage 62, the user-selected viewing plane is taken to be the viewing plane that was selected by the user. The rendering circuitry 40 renders a new animated series using the user-selected viewing plane. The process returns to stage 66 and the new animated series is displayed to the user. Stages 68, 60 and 66 may be repeated as often as is needed for the user to obtain a preferred view.

In the present embodiment, the viewing plane that is specified by the user at stage 68 is treated as fixed and is used in rendering without any automatic adjustment. In further embodiments, the viewing plane that is specified by the user at stage 68 may be used as a starting point for a further optimization of the viewing plane.

By automatically optimizing the viewing plane over all of the volumetric imaging data sets, a viewing plane may be obtained that is appropriate for viewing all of the images in an animated series. In contrast, it may be difficult to optimize a viewing plane to suit multiple image frames by manual adjustment.

Figure 6A:
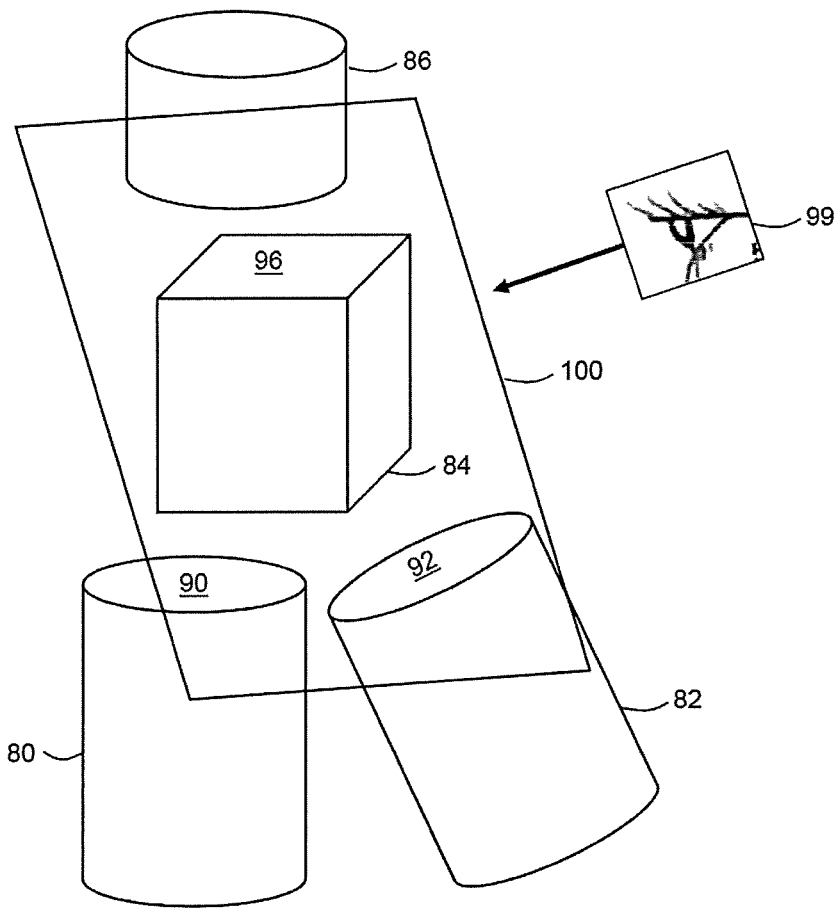
FIG. 6a is a schematic illustration of a planar reformat viewing plane.
Figure 6B:
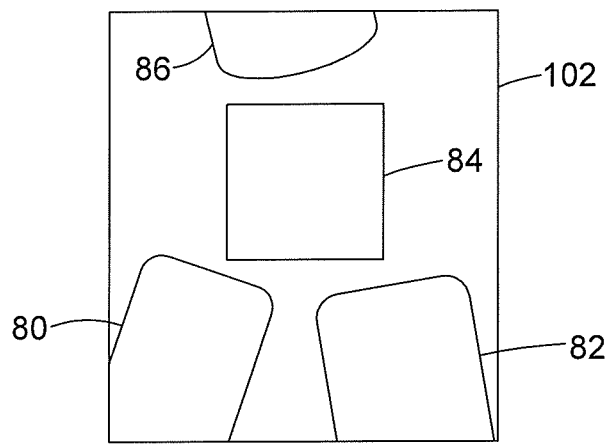
FIG. 6b is a schematic illustration of a planar reformat view as displayed to a user.

FIGS. 6a and 6b illustrate schematically an example of a plurality of bones for which volumetric imaging data has been obtained and a viewing plane used for rendering images of the plurality of bones.

FIG. 6a illustrates how a planar reformat viewing plane is placed on a 4D bone locked stack. FIG. 6a includes a schematic representation of four bones: the ulna 80, radius 82, lunate 84 and capitate 86. We note that, for simplicity, the bones are represented as basic geometric shapes instead of using a more realistic representation.

We consider an example of how the first embodiment of FIG. 3 may be applied to the bones shown in FIG. 6a. At stage 50, a 4D series is acquired which comprises a series of volumetric imaging data sets representative of different phases of motion of the ulna 80, radius 82, lunate 84 and capitate 86. At stage 52, the user selects the lunate 84 as the fixed bone $B_{lock}$. The user selects the ulna 80, radius 82 and capitate 86 as neighboring bones of interest [$B_1$, $B_2$, $B_3$]. The process moves on to stage 54.

At sub-stage 56, the pre-processing circuitry 36 extracts articular surfaces. In the example of FIG. 6a, six articular surfaces are extracted. The six articular surfaces may be grouped into three pairs. A first pair comprises an articular surface 90 of the ulna 80 facing the lunate 84, and a first articular surface of the lunate 84 which faces articular surface 90 of the ulna 80 (this articular surface is not visible in FIG. 6a). A second pair comprises an articular surface 92 of the radius 82 facing the lunate 84, and a second articular surface of the lunate 84 which faces articular surface 92 of the radius 82 (this articular surface is also not visible in FIG. 6a). A third pair comprises a third articular surface 96 of the lunate 84 facing the capitate 86, and an articular surface of the capitate (not visible in FIG. 6a) that faces the third articular surface 94 of the lunate 84.

At sub-stage 58, the pre-processing circuitry registers the volumetric imaging data sets together such that the lunate 84 remains static.

At stage 60, sub-stage 62 is used. The viewing circuitry 38 determines a viewing plane 100 by maximizing the sum of the projection of coordinate points of the six articular surfaces listed above across the volumetric imaging data sets. The projection of coordinate points on a given articular surface is only included in the sum when the viewing plane is within the extent of the bone in question. For example, projections of the coordinate points of the articular surface 90 of the ulna 80 onto the viewing surface 100 are only considered when the viewing surface 100 passes through the ulna 80.

The rendering circuitry 40 renders images from the volumetric imaging data sets using the determined viewing plane 100. The viewpoint from which the images are rendered is represented in FIG. 6a by an eye 99.

At stage 66, the rendering circuitry 40 displays the rendered images to the user. At stage 68, the user may manually adjust the determined viewing plane 100.

FIG. 6a is a schematic illustration of one of the rendered images, which may be described as a planar reformat view 102. The user sees a planar reformat view which cuts through the bones of interest, which in this case are the ulna 80, radius 82, lunate 84 and capitate 86.

In some circumstances, it may be difficult for a user to manually select a viewing plane that provides an acceptable view of the bones of interest. In this example, it may be difficult for a user to select a plane that provides a view of the first joint between the ulna and lunate, the second joint between the radius and lunate, and the third joint between the lunate and capitate.

By performing an optimization at sub-stage 62 based on all six articular surfaces, a viewing plane may be obtained that provides the best available view of all three joints, for example the best compromise view. In some embodiments, articular surfaces for different individual joints may be weighted such that one joint (for example ulna-lunate) is weighted more highly than another joint (for example, radius-lunate) in the determining of the viewing plane. In other embodiments, any suitable weighting may be used. In some circumstances, the weighting may be dependent on the type of motion being viewed.

We now consider an embodiment of the process of FIG. 3 in which a viewing surface comprising multiple planar sections is determined.

Stages 50, 52 and 54 (including sub-stages 56 and 58) are the same as described above with reference to the first embodiment of FIG. 3. On completion of stage 54, the pre-processing circuitry 36 passes the volumetric imaging data sets to the viewing circuitry 38. The volumetric imaging data sets have been labelled with regard to articular surfaces. The volumetric imaging data sets have been registered to each other such that a locked bone $B_{lock}$ remains static across the volumetric imaging data sets.

At stage 60, the process of the present embodiment moves to sub-stage 64. At sub-stage 64, the viewing circuitry 38 automatically determines a viewing surface to be used in rendering an animated series of frames using the volumetric imaging data sets.

Instead of the viewing surface comprising a single viewing plane as described above with reference to the first embodiment of FIG. 3 and FIGS. 6a and 6b, the viewing surface comprises several planar sections which are connected by at least one non-planar transition section.

Figure 7A:
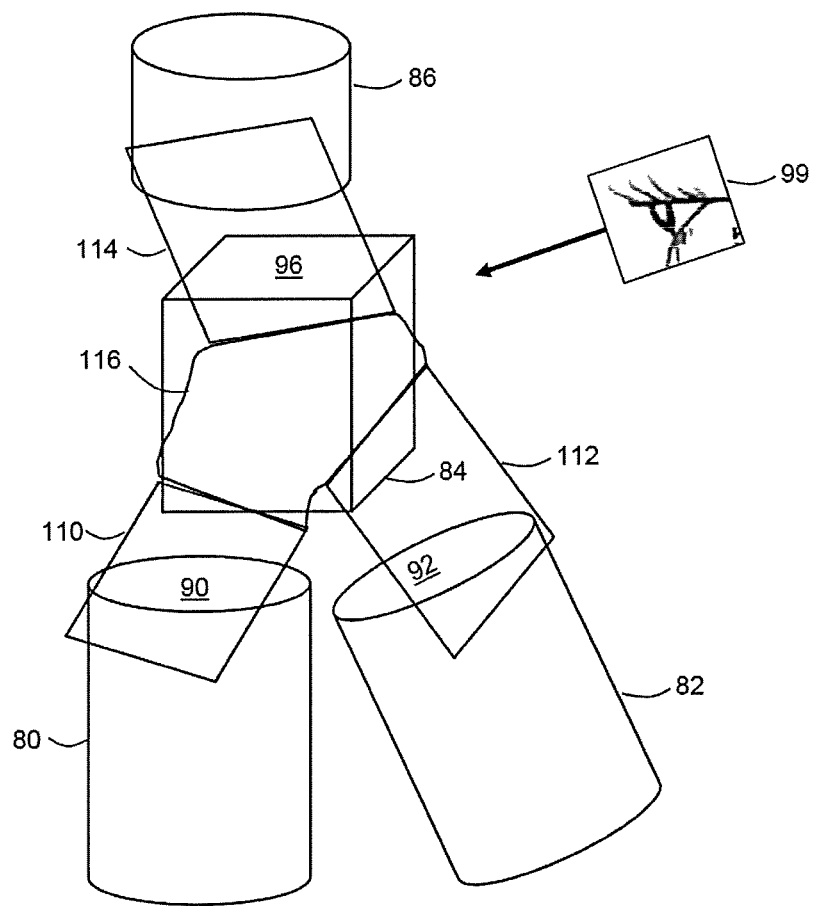
FIG. 7a is a schematic illustration of a curved and piecewise planar reformat viewing surface.
Figure 7B:
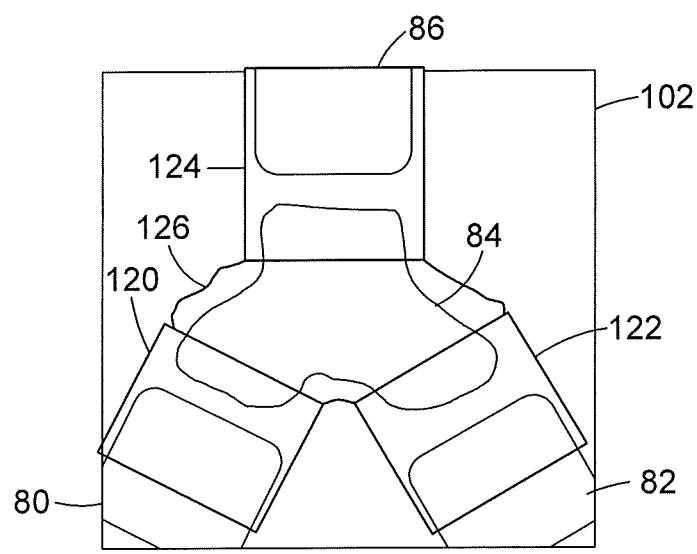
FIG. 7b is a schematic illustration of a curved and piecewise planar reformat view as displayed to a user.

As an example, we turn to FIGS. 7a and 7b. FIGS. 7a and 7b show the same ulna 80, radius 82, lunate 84 and capitate 86 as FIGS. 6a and 6b.

At sub-stage 64, the viewing circuitry 38 determines three individual planar sections 110, 112, 114 of the viewing surface.

We turn first to section 110. Section 110 is a flat 2D surface. Section 110 may be considered to be part of a flat 2D plane that passes through the centroid of the locked bone $B_{lock}$, which in this embodiment is the lunate 84. The position and extent of section 110 are such that section 110 passes through the joint between the ulna 80 and lunate 84.

The size and extent of planar section 110 are constrained such that the planar section 110 bounds the joint between the ulna 80 and lunate 84 and the relevant articular surfaces at a minimum.

The viewing circuitry 38 determines an orientation of planar section 110 based on the articular surface 90 of the ulna 80 that faces the lunate 84, and the articular surface (not shown) of the lunate 84 that faces articular surface 90. In the present embodiment, the viewing circuitry 38 determines the orientation of planar section 110 by maximizing a projection of articular surface 90 and its facing articular surface on planar section 110 across all of the volumetric imaging data sets. The orientation of planar section 110 may be determined in such a way as to provide a good view of the gap between the ulna 80 and lunate 84 across all of the frames rendered from the volumetric imaging data sets.

Planar section 112 is a further flat 2D surface, which is disjoint from planar section 110. Planar section 112 may be considered to be part of a further flat 2D plane that passes through the centroid of the locked bone $B_{lock}$, which in this embodiment is the lunate 84. The position and extent of planar section 112 are such that planar section 112 passes through the joint between the radius 82 and lunate 84. The size and extent of planar section 112 are constrained such that the planar section 112 bounds the joint between the radius 82 and lunate 84 and the relevant articular surfaces at a minimum.

The viewing circuitry 38 determines an orientation of planar section 112 based on the articular surface 92 of the radius 82 that faces the lunate 84, and the articular surface (not shown) of the lunate 84 that faces articular surface 92. In the present embodiment, the viewing circuitry 38 determines the orientation of planar section 112 by maximizing a projection of articular surface 92 and its facing articular surface on planar section 110 across all of the volumetric imaging data sets. The orientation of planar section 112 may be determined in such a way as to provide a good view of the gap between the radius 82 and lunate 84 across all of the frames rendered from the volumetric imaging data sets.

Planar section 114 is another flat 2D surface which is disjoint from planar section 110 and planar section 112. Planar section 114 may be considered to be part of another flat 2D plane that passes through the centroid of the locked bone $B_{lock}$, which in this embodiment is the lunate 84. The position and extent of planar section 114 are such that planar section 114 passes through the joint between the capitate 86 and lunate 84. The size and extent of planar section 114 are constrained such that the planar section 114 bounds the joint between the capitate 86 and lunate 84 and their articular surfaces at a minimum.

In the present embodiment, each of the planar sections 110, 112 and 114 is constrained to pass through the centroid of the locked bone $B_{lock}$. In other embodiments, any or none of the planar sections 110, 112 and 114 may be constrained to pass through the centroid.

In further embodiments, each of the planar sections 110, 112 and 114 may be configured to pass through a respective reference point within the locked bone $B_{lock}$, which may or may not be the centroid. Different reference points may apply to different planar sections 110, 112, 114. For example, a different reference point may be defined for each pair of articular surfaces. In further embodiments, the planar sections 110, 112, 114 may be constrained to intersect the locked bone. In other embodiments, no such constraint may be applied. The planar sections 110, 112 and 114 may be obtained by optimizing an intersection or projection without an additional constraint.

The viewing circuitry 38 determines an orientation of planar section 114 based on the articular surface 94 of the lunate 84 that faces the capitate 86, and the articular surface (not shown) of the capitate 86 that faces articular surface 96. In the present embodiment, the viewing circuitry 38 determines the orientation of planar section 114 by maximizing a projection of articular surface 96 and its facing articular surface on section 114 across all of the volumetric imaging data sets. The orientation of planar section 114 may be determined in such a way as to provide a good view of the gap between the capitate 86 and lunate 84 across all of the frames rendered from the volumetric imaging data sets.

The present embodiment differs from the first embodiment described with reference to FIG. 3 in that separate planar sections 110, 112, 114 are determined for the three joints. Each planar section is localized to a respective joint. The orientation of each planar section is determined based on articular surfaces of its corresponding joint. It may be the case that a different orientation is used for each of the joints. By using different orientations for each of the joints, a better view of the joints may be provided to a user. In particular, a better view may be provided when the movement of the joints is not all in the same plane, for example when a direction of motion of one joint occurs at an angle relative to a direction of motion of a neighboring joint.

In the present embodiment, the viewing surface comprises three planar sections. In other embodiments, the viewing surface may comprise any suitable number of planar sections, for example one planar section per joint. The planar sections may be disjoint. Any suitable method may be used to determine the position and extent of each of the planar sections.

In the present embodiment, the viewing circuitry 38 determines a non-planar transition section of the viewing surface. The non-planar transition section 116 is a curved surface which continuously connects the differently-oriented planar sections 110, 112, 114. In the present embodiment, the non-planar transition surface 116 is smoothly curved. The curvature of the non-planar transition section is determined based on the position and orientation of each of the planar sections 110, 112, 114.

A maximum extent of each of the planar sections 110, 112, 114 may be determined using a parameter limit on the non-planar transition section 116. For example, the maximum extent of each of the planar sections 110, 112, 114 may be determined based on a maximum amount of curvature of the non-planar transition section. By determining a maximum extent of each of the planar sections 110, 112, 114, it may be possible to maximize the planar regions of the viewing surfaces and thus minimize distortion around the regions of interest, which in this embodiment are the joints.

The viewing surface determines by the viewing circuitry 38 comprises three planar sections 110, 112, 114 and a non-planar transition section 116. The viewing surface may be described as a curved and piecewise planar reformat viewing surface, because parts of the viewing plane are curved and other parts are planar.

In other embodiments, the viewing surface may comprise any suitable number of planar sections. The viewing surface may comprise at least one non-planar transition section joining two or more of the planar sections.

In the embodiment described above, minimum and maximum extents of the planar sections 110, 112, 114 are determined based on the joint and on the curvature of the non-planar transition section 116. In other embodiments, any suitable method of determining an extent of each planar section may be used. In some embodiments, an extent of each planar section may be predetermined. In some embodiments, an extent of each planar section may be selected by a user.

The rendering circuitry 40 renders a respective image from each of the volumetric imaging data sets using the determined viewing surface. In the present embodiment, the rendering comprises a planar reformat. The planar reformat is performed using the viewing surface, which comprises a plurality of planar sections having different orientations, and at least one curved section.

It should be noted that the viewing surface of the present embodiment only comprises a curved part in areas that are of less anatomical interest. Planar sections of the viewing surface are used in the areas that are of most anatomical interest (corresponding to the articular surfaces).

At stage 66, the rendered images are displayed to the user as an animated series of frames. At stage 66, the user may manually orientate one or more of the planar sections 110, 112, 114, for example to obtain a view that the user prefers. If the user manually orientates one of the planar sections 110, 112, 114, the process returns to stage 60 for re-rendering.

FIG. 7b is a schematic illustration of an image 118 rendered from a volumetric imaging data set using a viewing surface comprising planar sections 110, 112, 114 and non-planar transition section 116. Regions of the image corresponding to planar sections 110, 112, 114 and non-planar transition section 116 are marked on the image as image sections 120, 122, 124 and image section 126 respectively.

Image section 126, which corresponds to non-planar transition section 116, provides a distorted image of the lunate. The image distortion results from the curvature of the non-planar transition section. The distortion may be referred to as a curve reformatting distortion. It may be expected that a curve reformatting distortion may occur where the viewing surface is non-planar. In the present embodiment, the viewing surface is generated such that curve reformatting distortions are only allowed in regions of less clinical interest, which in the present embodiment are non-joint regions. Bone articular surface information is used to avoid distorting clinically useful regions, i.e. joints.

In the present embodiment, image section 126 is highlighted when image 118 is displayed to the user. Image section 126 is highlighted to indicate to the user that anatomical structures that are present in image section 126 may be distorted due to image section 126 being rendering using a non-planar transitional section 116 of the viewing plane. The user is warned that distortion may be present.

Any suitable method may be used to highlight image section 126. For example, an overlay may be placed on image section 126. The overlay may comprise a color, a tint, or any other suitable image modification. In some embodiments, a magnitude of the highlighting (for example, an intensity of the color) is proportional to a degree of distortion. For example, a region of the viewing plane having higher curvature may be indicated on the image by stronger color.

In other embodiments, image sections 120, 122, 124 corresponding to the planar sections 110, 112, 114 are displayed. Instead of displaying a distorted image section 126 between image sections 120, 122, 124, the distorted image section 126 is omitted or obscured in the image 118. For example, the distorted image section 126 may be colored in black. Padding may be shown instead of an image.

In further embodiments, the planar viewing sections may be determined without a non-planar transitional section being determined. The viewing surface may comprise a set of disjoint planar viewing sections.

In embodiments in which the image sections 120, 122, 124 are shown with intervening regions being omitted or obscured, the image sections 120, 122, 124 may continue to be ordered anatomically. If the anatomical ordering is correct, the image 118 may be understood by a user even if only the joints in image sections 120, 122, 124 are shown without intervening anatomy being shown.

In some circumstances, the use of a curved and piecewise viewing surface as described may provide a better view of the individual joints than would be obtained by using a single viewing plane for all joints. However, the better view of the individual joints may be obtained at the expense of some distortion of the image of one or more transition regions between the individual joints.

In the embodiment described above, the planar viewing sections 110, 112, 114 are each determined separately, based on separate optimization processes. Each optimization process is based on a respective pair of articular surfaces.

In further embodiments, the determining of the planar viewing sections may be constrained. For example, the determining of the planar viewing sections may be constrained in order to control an amount of distortion that is allowed in the non-planar transition section 116.

A parameter may be introduced to the optimization which represents the distortion of the non-planar transition section 116, for example a parameter representing a degree of curvature of the non-planar transition section 116. Two or more planar viewing sections may be jointly optimized, for example by using the parameter to provide a constraint on distortion.

Embodiments described above may provide an automated method to estimate an optimal viewing plane. This viewing plane may display a reformat so as to not distort the anatomy (at least within the region of the joint). The anatomy may otherwise be minimally distorted. The viewing plane may be such as to provide a clinically useful view of a joint. The viewing plane may be estimated based on the appearance of a joint, for example the appearance of one or more gaps between bones, in a set of rendered frames that are representative of joint motion.

Embodiment described above may be used in the analysis of data from a 4D kinematic study of one or more joints. By analyzing data from a 4D kinematic study, multiple ligamentous injuries and instabilities may be studied. Examples of injuries that may be studied include injuries to the Triangular Fibrocartilage Complex (TFCC), subtalar luxation, Distal Radial Ulnar Joint Instability (DRUJI) and SLAC (scaphoid lunate advanced collapse) injuries. 4D kinematic studies of different joints may be performed, for example the wrist, ankle, shoulder, hip, elbow, acromioclavicular or temporomandibular joint.

In embodiments described above, a viewing surface is determined based on a plurality of volumetric imaging data sets. The determined viewing surface may be the viewing surface that provides the best view of a joint when many or all of the frames rendered from the volumetric imaging data sets are taken into consideration.

In other embodiments, a viewing surface may be determined based on a single volumetric imaging data set. In some embodiments, the pre-processing circuitry 36 determines two or more articular surfaces in a single volumetric imaging data set. The viewing circuitry 38 uses the articular surfaces to determine a viewing surface. In one embodiment, the viewing surface is a single planar surface, which may be referred to as a single viewing plane. In another embodiment, the viewing surface comprises a plurality of planar viewing sections. The rendering circuitry 40 renders an image from the volumetric imaging data set using the determined viewing surface.

Even in the case of a single volumetric imaging data set, it may be the case that a better view of the joint may be obtained by automatic optimization of the viewing surface than would be obtained manually. For example, the automated process may be used by a user who is inexperienced or in training.

In other embodiments, a viewing surface comprising multiple planar viewing sections is determined based on manual input from a user. For example, the user may determine and/or adjust each of the planar viewing sections to obtain a desired view. In some embodiments, the user may also determine or set limits on features of at least one non-planar transition section, for example by limiting curvature.

Particular bones and joints have been described above by way of example. In other embodiments, methods used above may be used on any suitable bones or joints. In some embodiments, an optimization process is extended to several joints (for example, all fingers in the hand). References to a bone above may include a prosthetic, for example an artificial hip or knee.

In embodiments described above, images are rendered by planar reformatting. In other embodiments, any suitable rendering methods may be used. In some embodiments, a slab is determined and used in rendering.

The rendering method used to render images may comprise at least one of multi-planar reconstruction (MPR), slab MPR, full-volume MPR, shaded volume rendering (SVR), SVR with cut planes defined by the bounds of a slab, global illumination.

Certain embodiments provide a medical imaging method comprising: acquiring a 4D data series capturing motion; indicating a bone to be locked spatially; and indicating a plurality of neighboring bones and/or joints of interest; and displaying the optimal viewing (piecewise) planar reformat with the 4D volumes cine to visualize motion.

The 4D data series may be a CT data series. Registration may be used to align all data with the bone indicated to be in a fixed position.

The centroid of the bone to be locked may be determined. Articular surfaces may be extracted for the bone to be locked and all the neighboring bones.

The optimal planar reformat may be determined by maximizing the projection of the sum of locations of the neighboring bones onto said plane.

Optimal planes may be determined for each joint separately by maximizing the projection of the sum of the locations of the articular surfaces of the neighboring bones individually. A smooth curved transition may be determined between the linear planes.

The articular surface may be extracted using an articular surface map (atlas), a bone landmark estimation method or a learned classification/detection method.

The distorted regions may be highlighted with an overlay with magnitude proportional to distortion. The overlay may comprise a color or tint overlay.

Padding may be shown in any of the distorted areas. The views may continue to be ordered anatomically so that if only joints are visible, then still can be understood.

Any combination of the orthogonal planes may be combined/viewed (orthogonal to plane of motion).

A parameter(s) may control the amount of distortion allowed in the curved portion and one or more of the set of planes may be jointly optimized.

Multiple bones/joints may be locked with respect to each other and the optimization may be extended to several joints (e.g. all fingers in the hand).

Certain embodiments provide a medical image processing apparatus comprising: processing circuitry configured to: acquire multiple time phases' medical images, accept a first body part included in the multiple time phases' medical images as a display target in a state that the display position is fixed through the multiple time phases, a second body part in the vicinity of the first body part as a display target, calculate a reference point of the first body part, identify an articular surface between the first body part and the second body part, and determine a viewing plane based on the reference point and the articular surface.

The processing circuitry may be further configured to: determine a plane as the viewing plane, which crosses the reference point of the first body part and includes at least part of the articular surface, through multiple time phases.

The processing circuitry may be further configured to: determine a plane as the viewing plane whose number of coordinate points which consists the articular surface was maximized.

The processing circuitry may be further configured to: calculate the reference point based on centroid of the first body part.

The processing circuitry may be further configured to: accept multiple second body parts as the display target, identify multiple articular surfaces between the first body part and the multiple second body parts, and determine the viewing plane based on a second viewing plane which includes the multiple articular surfaces and the reference point of the first body part.

The processing circuitry may be further configured to: determine the viewing plane based on a curved plane consisted by connecting the multiple second viewing planes continuously.

Registration of any appropriate medical imaging data to a suitable atlas may be performed, where medical includes veterinary. Medical imaging data may comprise, for example, CT, MR, ultrasound, rotational X-ray or cone beam CT data. Medical imaging data may comprise imaging data taken from one or more scans of a patient or other subject.

Whilst particular circuitries have been described herein, in alternative embodiments functionality of one or more of these circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whilst certain embodiments have been described, these embodiments have been presented by way of example only, and are not intended to limit the scope of the invention. Indeed the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. A medical image processing apparatus comprising processing circuitry configured to:
acquire a series of medical imaging data sets acquired across multiple time phases, the series of medical imaging data sets comprising at least a first medical image data set acquired for a first time phase and a second medical imaging data set acquired for a second time phase, wherein the medical imaging data sets are representative of a first body part and a second body part in the vicinity of the first body part, and wherein the first body part and second body part undergo relative motion across the multiple time phases; and
automatically determine a viewing surface for rendering a series of images from the medical imaging data sets, wherein the determining of the viewing surface is based on respective positions of the first body part and second body part in each of the series of medical imaging data sets, the respective positions comprising at least a first position of the first body part in the first medical imaging data set, a second position of the second body part in the first medical imaging data set, a third position of the first body part in the second medical imaging data set, and a fourth position of the second body part in the second medical imaging data set.

2. The medical image processing apparatus according to claim 1, wherein the first body part comprises a first bone of a joint, the second body part comprises a second bone of the joint, and the relative motion of the first body part and second body part comprises a motion of the joint.

3. The medical image processing apparatus according to claim 1, wherein the series of medical imaging data sets are aligned with each other such that a display position of the first body part is fixed throughout the series of images.

4. The medical image processing apparatus according to claim 1, wherein the processing circuitry is further configured to determine a reference point of the first body part, and wherein the determining of the viewing surface is based on the reference point.

5. The medical image processing apparatus according to claim 4, wherein the reference point is based on a centroid of the first body part.

6. The medical image processing apparatus according to claim 1, wherein the processing circuitry is further configured to identify at least one articular surface between the first body part and the second body part, and wherein the determining of the viewing surface is based on the at least one articular surface.

7. The medical image processing apparatus according to claim 6, wherein the at least one articular surface comprises an articular surface of the first bone and an articular surface of the second bone, and wherein determining the at least one articular surface comprises at least one of: registering the first bone and second bone to an atlas, estimation of at least one bone landmark, a learned classification method, a regression method, and image analysis.

8. The medical image processing apparatus according to claim 6, wherein the viewing surface comprises a plane that intersects a reference point of the first body part and includes at least part of the at least one articular surface across the multiple time phases.

9. The medical image processing apparatus according to claim 6, wherein the viewing surface comprises a plane, and wherein determining the viewing surface comprises maximising at least one of a) and b):
a) a projection of coordinate points on the at least one articular surface onto the plane; and
b) a number of coordinate points in the multiple image data sets at which the plane intersects the at least one articular surface.

10. A medical image processing apparatus according to claim 6, wherein the series of medical image data sets is representative of multiple second body parts undergoing relative motion across the medical image data sets; and wherein the viewing surface comprises a plurality of planar viewing sections, each corresponding to a respective one of the multiple second body parts.

11. A medical image processing apparatus according to claim 10, wherein the planar viewing sections have different orientations, and wherein the processing circuitry is further configured to render at least one image from the medical image data sets using the viewing surface, such that the rendered image comprises image sections obtained using differently-orientated planar viewing sections.

12. A medical image processing apparatus according to claim 10, wherein the processing circuitry is configured to identify multiple articular surfaces, the multiple articular surfaces comprising a respective at least one articular surface between each of the multiple second body parts and the first body part; and
wherein determining the viewing surface comprises determining each of the planar viewing sections based on the reference point of the first body part and on the at least one articular surface between the first body part and the second body part corresponding to that planar viewing section.

13. A medical image processing apparatus according to claim 10, wherein the viewing surface further comprises a curved transition section connecting at least two of the planar viewing sections in a continuous manner.

14. A medical image processing apparatus according to claim 13, wherein the determining of the planar viewing sections and/or the at least curved transitional section of the viewing surface is such as to constrain an amount of distortion in at least one image rendered using the viewing surface.

15. A medical image processing apparatus according to claim 13, wherein the processing circuitry is further configured to render using the viewing surface at least one image in which a part of the image corresponding to the curved transition section is highlighted, thereby to draw a user's attention to an anatomical distortion caused by the curvature of the curved transition section.

16. A medical image processing apparatus according to claim 10, wherein the processing circuitry is further configured to render using the viewing surface at least one image in which at least one part of the image corresponding to a region between the planar viewing sections is obscured and/or omitted.

17. An apparatus according to claim 1, wherein at least one of a) and b):
a) the processing circuitry is configured to receive from a user an indication of the first body part and/or an indication of the second body part; and
b) the processing circuitry is configured to determine an indication of the first body part and/or an indication of the second body part by at least one of: registering at least one of the medical imaging data sets to an atlas, estimation of at least one bone landmark in at least one of the medical imaging data sets, and applying a learned classification method to at least one of the medical imaging data sets.

18. A medical image processing method comprising:

acquiring a series of medical imaging data sets acquired across multiple time phases, the series of medical imaging data sets comprising at least a first medical image data set acquired for a first time phase and a second medical imaging data set acquired for a second time phase, wherein the medical images are representative of a first body part and a second body part in the vicinity of the first body part, and wherein the first body part and second body part undergo relative motion across the multiple time phases; and automatically determining a viewing surface for rendering a series of images from the medical imaging data sets, wherein the determining of the viewing surface is based on respective positions of the first body part and second body part in each of the series of medical imaging data sets, the respective positions comprising at least a first position of the first body part in the first medical imaging data set, a second position of the second body part in the first medical imaging data set, a third position of the first body part in the second medical imaging data set, and a fourth position of the second body part in the second medical imaging data set.

* * * * *